United States Patent
Almutairi et al.

(10) Patent No.: US 9,522,289 B2
(45) Date of Patent: Dec. 20, 2016

(54) SELECTIVE FAT REMOVAL USING PHOTOTHERMAL HEATING

(71) Applicants: The Regents of the University of California, Oakland, CA (US); eLux Medical, Inc., San Diego, CA (US)

(72) Inventors: Adah Almutairi, La Jolla, CA (US); Khalid Almutairi, La Jolla, CA (US)

(73) Assignees: THE REGENTS OF THE UNIVERSITY OF CALIFORNIA, Oakland, CA (US); eLUX MEDICAL, INC., San Diego, CA (US)

( * ) Notice: Subject to any disclaimer, the term of this patent is extended or adjusted under 35 U.S.C. 154(b) by 0 days.

(21) Appl. No.: 14/757,872

(22) Filed: Dec. 23, 2015

(65) Prior Publication Data

US 2016/0236005 A1     Aug. 18, 2016

Related U.S. Application Data

(63) Continuation-in-part of application No. 14/464,629, filed on Aug. 20, 2014, now Pat. No. 9,333,259, which
(Continued)

(51) Int. Cl.
*A61B 18/04* (2006.01)
*A61N 5/06* (2006.01)
(Continued)

(52) U.S. Cl.
CPC ........... *A61N 5/062* (2013.01); *A61K 41/0052* (2013.01); *A61M 1/008* (2013.01);
(Continued)

(58) Field of Classification Search
CPC ....... A61B 18/20; A61B 18/04; A61B 18/203; A61B 18/28; A61B 2018/00464; A61M 2202/08; A61N 2005/067; A61N 2005/0659; A61N 5/062; A61K 41/0052
(Continued)

(56) References Cited

U.S. PATENT DOCUMENTS

| 5,226,907 A | 7/1993 | Tankovich |
| 5,425,728 A | 6/1995 | Tankovich |

(Continued)

FOREIGN PATENT DOCUMENTS

| WO | 2009108933 A2 | 9/2009 |

OTHER PUBLICATIONS

Samim, M., et al., "Synthesis and characterization of gold nanorods and their application for photothermal cell lamage", International Journal of Nanomedicine, 2011:6 1825-1831.
(Continued)

*Primary Examiner* — Michael Peffley
*Assistant Examiner* — Thomas Giuliani
(74) *Attorney, Agent, or Firm* — Eleanor Musick; Musick Davison LLP

(57) ABSTRACT

A system and method are provided for minimally-invasive selective fat removal from a target area by injecting the area with a solution of photo-absorbing nanoparticles and irradiating the injected area with a beam of near infrared (NIR) light. The NIR emission wavelength excites the nanoparticles to melt fat within the target area so that the liquefied fat can be aspirated from the target area. The nanoparticles may be gold nanorods having aspect ratios selected to produce surface plasmon resonance when irradiated with NIR light around 800 nm.

26 Claims, 11 Drawing Sheets

Related U.S. Application Data is a continuation of application No. 14/379,488, filed as application No. PCT/US2013/040219 on May 8, 2013, now Pat. No. 9,333,258.

(60) Provisional application No. 61/644,328, filed on May 8, 2012.

(51) Int. Cl.
*A61K 41/00* (2006.01)
*A61M 1/00* (2006.01)
*A61N 5/067* (2006.01)

(52) U.S. Cl.
CPC .... *A61M 2202/08* (2013.01); *A61N 2005/067* (2013.01); *A61N 2005/0659* (2013.01)

(58) Field of Classification Search
USPC .......... 606/27, 33; 607/89, 100; 604/20, 542
See application file for complete search history.

(56) References Cited

U.S. PATENT DOCUMENTS

| | | | |
|---|---|---|---|
| 5,817,089 | A | 10/1998 | Tankovich et al. |
| 6,063,074 | A | 5/2000 | Tankovich |
| 6,126,655 | A | 10/2000 | Domankevitz et al. |
| 6,152,917 | A | 11/2000 | Tankovich |
| 6,165,440 | A | 12/2000 | Esenaliev |
| 6,302,863 | B1 | 10/2001 | Tankovich |
| 6,344,272 | B1 | 2/2002 | Oldenburg et al. |
| 6,350,261 | B1 | 2/2002 | Domankevitz et al. |
| 6,530,944 | B2 | 3/2003 | West et al. |
| 6,605,080 | B1 | 8/2003 | Altshuler et al. |
| 6,685,927 | B2 | 2/2004 | Sumian et al. |
| 6,685,986 | B2 | 2/2004 | Oldenburg et al. |
| 7,060,061 | B2 | 6/2006 | Altshuler et al. |
| 7,276,088 | B2 | 10/2007 | Huang et al. |
| 7,371,457 | B2 | 5/2008 | Oldenburg et al. |
| 7,438,411 | B2 | 10/2008 | Payne et al. |
| 7,891,362 | B2 | 2/2011 | Domankevitz et al. |
| 8,057,418 | B2 | 11/2011 | Korbling et al. |
| 8,357,146 | B2* | 1/2013 | Hennings ............... A61B 18/22 604/542 |
| 8,801,690 | B2 | 8/2014 | Peyman |
| 8,840,608 | B2 | 9/2014 | Anderson et al. |
| 8,915,948 | B2 | 12/2014 | Altshuler et al. |
| 2004/0006328 | A1 | 1/2004 | Anderson |
| 2005/0175649 | A1 | 8/2005 | Disalvo et al. |
| 2005/0203495 | A1 | 9/2005 | Malak |
| 2007/0060989 | A1 | 3/2007 | Deem et al. |
| 2007/0208400 | A1 | 9/2007 | Nadkarni et al. |
| 2008/0241262 | A1 | 10/2008 | Lee et al. |
| 2008/0279946 | A1 | 11/2008 | Hainfeld |
| 2010/0057068 | A1* | 3/2010 | Lee ..................... A61K 41/0052 606/27 |
| 2010/0294952 | A1 | 11/2010 | Mirkin et al. |
| 2011/0052672 | A1 | 3/2011 | Krishnan et al. |
| 2011/0059023 | A1 | 3/2011 | Tunnell et al. |
| 2011/0182805 | A1 | 7/2011 | DeSimone et al. |
| 2011/0306956 | A1 | 12/2011 | Islam |
| 2012/0059307 | A1* | 3/2012 | Harris ................... A61K 8/0245 604/20 |
| 2013/0225901 | A1 | 8/2013 | Krishnan et al. |
| 2014/0005593 | A1 | 1/2014 | Harris et al. |
| 2014/0012162 | A1 | 1/2014 | Harris et al. |
| 2014/0012163 | A1 | 1/2014 | Harris et al. |
| 2014/0012183 | A1 | 1/2014 | Harris et al. |
| 2014/0358068 | A1 | 12/2014 | Almutairi et al. |
| 2015/0018812 | A1 | 1/2015 | Almutairi et al. |

OTHER PUBLICATIONS

Zhan, Q. et al., Using 915 nm Laser Excited TM3+/Er3+/Ho3+-Doped NaYbF4 Upconversion Nanoparticles for in Vitro and Deeper in Vivo Bioimaging without Overheating Irradiation, ACS Nano, 2011, vol. 5, No. 5:3744-3757.

Zijlstra, P., "Photothermal properties of gold nanorods and their application to five-dimensional optical recording", Thesis, Centre for Micro-Photonics, Swinburne University of Technology (AU), Jun. 2009, pp. 8, 26, 61 and 101.

PCT/US2013/040219 International Search Report and Written Opinion, Jul. 24, 2013, 7 pages.

Bawa, R., "Nanoparticle-based Therapeutics in Humans: A Survey", Nanotechnology Law & Business, Summer 2008, pp. 135-155.

Yanina, I.Y., et al., "Effect of bacterial lectin on acceleration of fat cell lipolysis at in vitro diode laser treatment using encapsulated ICG", Saratov Fall Meeting 2011: Optical Technologies in Biophysics and Medicine XIII, 2012, Proc. of SPIE vol. 8337, pp. 83370F-1-83370F-7.

Tong, L., et al., "Gold nanorods as contrast agents for biological imaging: optical properties, surface conjugation, and photothermal effects", Photochem Photobiol. 2009; 85(1): 21. doi:10.1111/j.1751-1097.2008.00507.x.

Yanina, I.Y., et al., "Fat tissue histological study at indocyanine green-mediated photothermal/photodynamic treatment of skin in vivo", Journal of Biomedical Optics, May 2012, vol. 17(5), pp. 058002-1 to 058002-9.

Anderson, R.R., et al., "Selective Photothermolysis: Precise Microsurgery by Selective Absorption of Pulsed Radiation", Science, New Series, Apr. 29, 1983, 220(4596): 524-527.

Chen, J., et al., "Immuno Gold Nanocages with Tailored Optical Propertoes for Targeted Photothermal Destruction of Cancer Cells", Nano Lett. May 2007; 7(5): 1318-1322.

Cox, B., "Optics in Medicine: Introduction to Laser-Tissue Interactions", Oct. 2013, University College of London, Dep't of Medical Physics and Biomed Engineering, Course Notes, published on-line; pp. 3-64.

Chertok, B., et al., "Drug Delivery Interfaces in the 21st Century: From Science Fiction Ideas to Viable Technologies", Mol Pharm. Oct. 7, 2013; 10(10): doi.10.1021/mp4003283.

Farokhzad, O.C., et al., "Impact of Nanotechnology on Drug Delivery", ACS NANO, Jan. 27, 2009; 3(1):16-20.

Halachmi, S. et al., "Low-fluence vs. standard fluence hair removal: A contralateral control non-inferiority study", J. Cosm. Laser Ther., 2012; 14:2-6.

Ichikawa, K., et al., "Histologic Evaluation of the Pulsed Nd:YAG Laser for Laser Lipolysis", Lasers in Surg. Med., 2005; 36:43-46.

Katz, B. et al., "Laser-assisted lipolysis: A report on complications", J. Cosm. Laser Ther., 2008, iFirst Article, 1-3.

Majdabadi, A. et al., "Analysis of Laser-Fat Interaction Through Comparing 980 nm Diode Laser with 1064 nm Nd: YAG Laser", J Skin Stem Cell; May 2014; 1(1):e17793 (6 pages).

McBean, J.C., et al., "Laser Lipolysis: An Update", J. Clin. Aesth. Dermatol., Jul. 2011; 4(7):25-34.

De Felice, E., "Shedding light: laser physics and mechanism of action", Phlebology, 2010; 25:11-28.

Mordon, S., et al., "Laser lipolysis versus traditional liposuction for fat removal", Exp. Rev. Med. Devices, 2009, 6(6):677-688.

Neira, R., et al., "Fat Liquefaction: Effect of Low-Level Laser Energy on Adipose Tissue", Plastic and Reconstr. Surg., Sep. 1, 2002, 110(3):912-925.

O'Dey, D., et al., "Ablative Targeting of Fatty-Tissue Using a High-Powered Diode Laser", Lasers in Surg. Med., 2008; 10:100-105.

Palm, M.D., et al., "Laser Lipolysis: Current Practices", Semin Cutan Med. Surg., 2009, 28:212-219.

Parlette, E.G., et al., "Laser-Assisted Liposuction: Here's the Skinny", Semin Cutan Med. Surg., 2008, 27:259-263.

Peer, D., et al., "Nanocarriers as an emerging platform for cancer therapy", Nat. Nanotech., Dec. 2007; 2:751-760.

Perez-Juste, J., et al., "Gold nanorods: Synthesis, characterization and applications", Coordination Chemistry Reviews, Apr. 1, 2005; 249: 1870-1901.

Prausnitz, M.R., et al., "Transdermal drug delivery", Nat. Biotech. Nov. 2008; 26(11):1261-1268.

(56) References Cited

OTHER PUBLICATIONS

Sklar, L.R., et al., "Laser Assisted Drug Delivery: A Review of an Evolving Technology", Lasers Surg. Med., 2014, 46:249-262.
Steiner, R., "Laser-Tissue Interactions", in Laser and IPL Technology in Dermatology and Aesthetic Medicine, C. Raulin and S. Karsai (eds.), Springer-Verlag Berlin Heidelberg, 2011, pp. 23-36.
Tagliolatto, S., et al., "Laserlipolysis: update and literature review", Surg Cosmet Dermatol, 2012; 4(2):164-174.
Youn, J-I., et al., "Ablation efficiency and relative thermal confinement measurements using wavelengths 1,064, 1,320, and 1,444 nm for laser-assisted lipolysis", Lasers Med Sci., 2013.
Yanina, I., et al., "Fat tissue histological study at NIR laser treatment of the skin in vivo", Medical Laser Applications and Laser-Tissue Interactions V, SPIE, Jun. 9, 2011, 8092(1):1-8.
Terentyuk, G.S., et al., "Laser-induced tissue hyperthermia mediated by gold nanoparticles: toward cancer phototherapy", J Biomed Opt., Apr. 27, 2009, 14(2): 021016-1- 021016-9.
EP13786914.5 Supplementary European Search Report and Written Opinion, Jan. 18, 2016, 9 pages.

\* cited by examiner

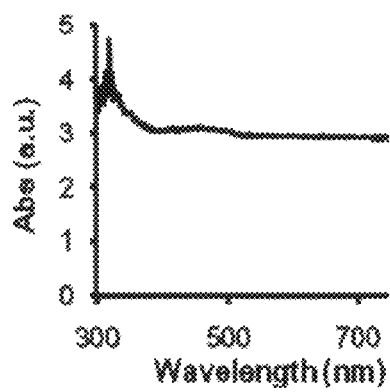 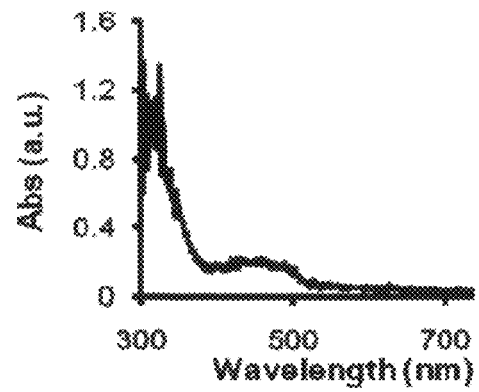
FIG. 3A FIG. 3B
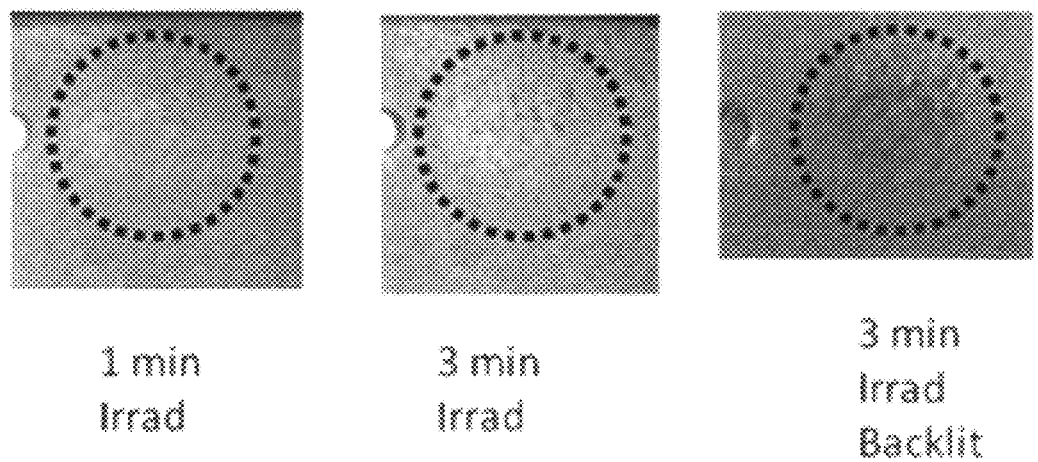
1 min Irrad 3 min Irrad 3 min Irrad Backlit
FIG. 4

NO LASER  NO LASER
GNR       NO GNR

LASER   LASER
GNR     NO GNR

NO LASER
NO GNR

LASER
GNR

SELECTIVE FAT REMOVAL USING PHOTOTHERMAL HEATING

RELATED APPLICATIONS

This application is continuation-in-part of application Ser. No. 14/464,629, filed Aug. 20, 2014, now U.S. Pat. No. 9,333,529, which is a continuation of application Ser. No. 14/379,488, filed Aug. 18, 2014, now U.S. Pat. No. 9,333,258, which is a 371 national stage filing of International Application No. PCT/US2013/040219, filed May 8, 2013, which claims the benefit of the priority of Application No. 61/644,328, filed May 8, 2012, which is incorporated herein by reference in its entirety.

FIELD OF THE INVENTION

The invention relates to a system, kit and method for reduction of fatty tissue in the body, and more particularly to removal of fatty tissue using near infrared laser light to irradiate nanoparticles injected into the tissue.

BACKGROUND OF THE INVENTION

Liposuction evolved from work in the late 1960s from surgeons in Europe using primitive curettage techniques which were largely ignored, as they achieved irregular results with significant morbidity and bleeding. Modern liposuction first burst on the scene in a presentation by the French surgeon, Dr Yves-Gerard Illouz, in 1982. The "Illouz Method" featured a technique of suction-assisted lipolysis after tumesing or infusing fluid into tissues using blunt cannulas and high-vacuum suction and demonstrated both reproducible good results and low morbidity. During the 1980s, many United States surgeons experimented with liposuction, developing variations, and achieving mixed results. Most commonly, liposuction is performed on the abdomen and thighs in women, and the abdomen and flanks in men. According to the most recent statistics by the American Society for Aesthetic Plastic Surgery, liposuction, including conventional suction-assisted lipectomy (SAL), ultrasound-assisted liposuction (UAL), and laser-assisted liposuction (LAL), is the most common aesthetic procedure performed by plastic surgeons in the United States. However, these procedures are often associated with secondary complications such as contour deformities, irregular lumpy appearance, and excess skin, leading to patient dissatisfaction.

Traditional liposuction relies on two techniques. The first technique employs a sharp, relatively large diameter (3 mm-5 mm) cannula that is manually manipulated to mechanically break fat down and while applying suction to remove the separated fat. A variation of this vacuum assisted technique is a mechanically powered cannula that reduces the surgeon's fatigue during large surface area liposuction procedures.

The second technique utilizes ultrasonic waves via a vibrating cannula, this technique is mechanical in its nature and significantly reduces the surgeon's fatigue factor. This technique induces the same or worse mechanical trauma to the tissues. Both techniques require significant amounts of fluid, known as a "tumescent solution," to be injected into the body to emulsify the fat, facilitating the removal of large volumes of fat while reducing blood loss and delivering a local anesthetic (lidocaine) to provide post-operative pain relief. While generally safe, lidocaine can be toxic, leading to serious complications, and even death.

A problem with the probes used in existing liposuction procedures is the generation of significant amounts of heat at the distal tip of the probe, which can exceed the temperature required for melting the fatty tissue. This excess heat can result in burning of tissue, damaging muscles or blood vessels, and even penetrating membranes such as the skin or the peritoneum that covers most of the intra-abdominal organs.

Alternative methods have been disclosed which exploit laser energy to remove unwanted fat, known as laser-assisted liposuction (LAL). Current FDA-approved technologies for LAL rely predominantly on wavelengths around or beyond 1000 nm, where water absorbs and emits heat. As a result, these methods require the insertion of laser probes into the subcutaneous tissue to liquefy small volumes of fat. Because of the point source nature of the heating device, results are not uniform, and surrounding subcutaneous tissue, such as muscle and fibrous connective tissues, may also be heated. Further, because such systems rely on endogenous chromophores such as water or hemoglobin, their concentration is fixed.

U.S. Pat. Nos. 6,605,080 and 7,060,061, both issued to Altshuler, et al. represent an alternative approach in which laser energy is externally applied to the skin to heat and melt fat tissue in epidermis and subcutaneous layers below. These patents disclose the use of near- to mid-infrared radiation wavelengths that are preferentially absorbed by lipid cells to heat-liquefy fat cells, after which the lipid pool may be removed from the subcutaneous area by aspiration. The need to fine-tune the laser wavelength for preferential absorption by the lipid cells, as well as the considerable heat generation that results from the techniques, e.g., up to 70° C., at or in the fat tissue, require use of a cooling mechanism to prevent skin damage or permanent scarring. These methods present other limitations and potential adverse thermal effects on tissue above the lipid-rich tissue under treatment, including blistering, peeling, and depigmentation.

U.S. Pat. No. 8,357,146 of Hennings discloses a LAL device and method in which wavelengths of pulsed laser radiation that are preferentially absorbed by lipid cells are applied directly to the tissue by inserting a fiber optic probe into the target area. As in Altschuler's method, the direct absorption of the laser energy heats the fat, however, this heating is augmented by a coating on the optical fiber that absorbs the laser energy and acts as a hot tip, or "char", to ablate and disrupt tissue. This high temperature char creates a risk of accidental damage to surrounding tissue.

U.S. Pat. No. 8,430,919 of Bornstein discloses a lipolysis method in which the skin over the target site is optically irradiated with two different wavelengths of light, one in the near infrared (NIR) region, the other in the infrared range, to modulate biochemical processes of adipocytes in the target site. In order to achieve the desired degree of fat removal, the duration of the treatment must be relatively long, from one to two hours, during which the patient must remain virtually motionless. Unless a sedative or general anesthesia has been administered to calm the patient, physical and psychological discomfort can ensue.

NIR (700-950 nm) is preferable to other types of light for therapeutic use in biological systems because NIR light can pass through blood and tissue to depths of several inches. However, very few organic chromophores absorb in this region, and even fewer are capable of converting the absorbed energy into a chemical or thermal response that can be used to trigger drug release. A few years ago, gold nanostructures (shells, particles, rods, and cages) emerged as useful agents for photothermal therapy after they were shown to have strong absorption in the NIR region (four to five times higher than conventional photo-absorbing dyes) as well as tunable optical resonances. The strong absorption enables effective laser therapy at relatively low laser energies, rendering such therapy methods minimally invasive.

Laser photothermal therapy of cancer with the use of gold nanoparticles immunotargeted to molecular markers has been reported as being effective to selectively kill cancer cells at lower laser powers than those needed to kill healthy cells. (X. Huang, et al., "Determination of the Minimum Temperature Required for Selective Photothermal Destruction of Cancer Cells with the Use of Immunotargeted Gold Nanoparticles", *Photochemistry and Photobiology*, 2006, 82:412-417.) Gold nanoparticles absorb light efficiently in the visible region due to coherent oscillations of metal conduction band electrons in strong resonance with visible frequencies of light, a phenomenon known as "surface plasmon resonance" or "SPR". Photoexcitation of metal nanostructures results in the formation of a heated electron gas that cools rapidly, e.g., within 1 ps, by exchanging energy with the nanoparticle lattice. The nanoparticle lattice, in turn, rapidly exchanges energy with the surrounding medium on the timescale of 100 ps, causing localized heating. This rapid energy conversion and dissipation can be achieved by using light radiation with a frequency that strongly overlaps the nanoparticle absorption band.

U.S. Patent Publication 2012/0059307 of Harris et al. discloses a method of selective thermomodulation in tissue that applies nanoparticles to a target tissue region that is then irradiated with laser light to induce thermal damage to destroy or remove the tissue by ablation. Ablation involves the cutting or removal of tissue by fracture of chemical bonds through phase transitions consisting of vaporization, molecular fragmentation, and/or void formation, i.e., a violent, destructive process. (See, e.g., A. Vogel and V. Venugopalan, "Mechanisms of Pulsed Laser Ablation of Biological Tissues", *Chem. Rev.* 2003, 103, 577-644.) Harris' et al.'s target tissue includes hair follicles, sebaceous glands, and unwanted or diseased vasculature, where destruction (necrosis or apoptosis) of the target tissue is the goal. However, for applications where actual destruction of the tissue is not desirable, this approach is not appropriate.

The conditions for irradiation as well as the nanoparticle characteristics are critical for obtaining the necessary control for providing effective treatment while avoiding tissue damage. Nanorods exhibit cylindrical symmetry, and simple changes in particle symmetry can significantly alter SPR characteristics. The NIR absorption maximum of metal nanostructures can be modulated by changing their size, shape and aggregation. GNRs have two plasmon absorption peaks, exhibiting transverse and longitudinal surface plasmon resonances that correspond to electron oscillations perpendicular and parallel to the rod length direction, respectively. The longitudinal surface plasmon wavelengths are tunable from the visible to infrared regions. The effectiveness of GNRs as photothermal therapeutic agents is strongly dependent on their scattering and absorption cross-sections—large absorption cross sections with small scattering losses allow for photothermal therapy with a minimal laser dosage. In addition, the longitudinal surface plasmon wavelengths of GNRs are preferably within the spectral range of 650-900 nm. Light irradiation in this region can penetrate more deeply into tissues and cause less photodamage than UV-visible irradiation. Therefore, the ability to tailor both scattering and absorption of GNRs with different longitudinal surface plasmon wavelengths is important for therapeutic applications.

BRIEF SUMMARY

In an exemplary embodiment, the apparatus and method of the present invention combines near infrared (NIR) light exposure and a solution of gold nanorods (GNRs) that may be injected into the treatment target in order to selectively and gently heat fat in the target area. The low power NIR light harmlessly penetrates the skin and overlying tissue to be absorbed only by the GNRs. The excited GNRs generate heat, melting the fat and tightening the skin. The liquefied melted fat can be removed with a syringe or fine cannula.

According to an embodiment of the invention, a GNR solution energized by NIR laser exposure heats adipose tissue by surface plasmon resonance (SPR). The wavelength absorbed can be tuned by altering particle shape, size, geometry, and aspect ratio. This absorption causes gold electrons to oscillate with the frequency of the electromagnetic field, generating heat with extremely high efficiency. Photothermal conversion through SPR allows for rapid but controlled localized heating that is more selective than other methods of heating, and is thus suitable for heating of soft tissue. Photothermal conversion through SPR takes advantage of the difference in thermal relaxation rates between fat and surrounding tissues to allow selective photothermolysis. Because fat has a lower thermal conductivity (0.631 W m$^{-1}$ K$^{-1}$ vs. 0.23 W m$^{-1}$ K$^{-1}$), (13, 14) as well as a lower specific heat capacity (4.18 kJ g$^{-1}$ K$^{-1}$ vs. 2.3 kJ g$^{-1}$ K$^{-1}$) than water, it heats faster and dissipates heat more slowly, enhancing the selectivity of heating enabled by injection of the GNR solution into the adipose layer. Heating by this mechanism softens and loosens adipose tissue, facilitating removal with minimal trauma. Only surgeon-defined regions, where the GNR solution is infused, absorb laser energy, minimizing the potential for damage to surrounding tissues.

In one aspect of the invention, a system is provided for minimally-invasive removal of fat within a target area, including a solution of photo-absorbing nanoparticles; means for injecting the solution into the target area; a near infrared light source for delivering a beam of light to the target area; at least one beam adjusting optical element for controlling focus and beam size within the target area; a system controller for providing control signals to the infrared light source, wherein the control signals comprise selection of an emission wavelength, an emission intensity and an exposure duration, and wherein the emission wavelength is adapted to excite the nanoparticles to melt fat within the target area; and means for extracting melted fat from the target area. In a preferred embodiment, the nanoparticles are biocompatible, and photo-absorption in the nanoparticles is mediated by surface plasmon resonance. The nanoparticles may be selected to absorb in the near infrared range (700-900 nm) and in the preferred embodiment are gold nanorods. The gold nanorods may have an aspect ratio in the range of 1:3-1:5, with an axial diameter of approximately 10 nm and a longitudinal diameter in the range of 9-50 nm. The gold nanorods may be suspended in water at a concentration of around $3\times10^{11}$-$3\times10^{12}$ GNR/mL. The near infrared light source may be a NIR laser having tunable power and/or wavelength, and further comprising beam adjusting optical means for control of beam size at the target area and may emit light within the wavelength range of 600 nm to 950 nm, more preferably in the range of 700 nm to 900 nm, and most preferably around 800 nm.

In another aspect of the invention, a photothermal method is provided for in vivo fat removal by melting the fat using the system that includes a solution of photo-absorbing nanoparticles; means for injecting the solution into the target area; a near infrared light source for delivering a beam of light to the target area; at least one beam adjusting optical element for controlling focus and beam size within the target area; a system controller for providing control signals to the infrared light source, wherein the control signals comprise selection of an emission wavelength, an emission intensity and an exposure duration, and wherein the emission wavelength is adapted to excite the nanoparticles to melt fat within the target area; and means for extracting melted fat from the target area.

In still another aspect of the invention, a method is provide for inducing skin tightening around regions from which adipose tissue has been removed using the system that includes a solution of photo-absorbing nanoparticles; means for injecting the solution into the target area; a near infrared light source for delivering a beam of light to the target area; at least one beam adjusting optical element for controlling focus and beam size within the target area; a system controller for providing control signals to the infrared light source, wherein the control signals comprise selection of an emission wavelength, an emission intensity and an exposure duration, and wherein the emission wavelength is adapted to excite the nanoparticles to melt fat within the target area; and means for extracting melted fat from the target area.

Another aspect of the invention is a photothermal agent for melting fat and skin tightening comprising photo-absorbing nanoparticles suspended in a solution, wherein the photo-absorbing nanoparticles are adapted to convert NIR light energy into fat-melting heat in a target area in which the nanoparticles have been injected. In a preferred embodiment, the nanoparticles are gold nanorods.

Yet another aspect of the invention is a kit for in vivo photothermal removal of fat in a target area irradiated by NIR light energy, the kit including photo-absorbing nanoparticles suspended in a solution, wherein the photo-absorbing nanoparticles are adapted to convert NIR light energy into heat having a temperature that melts fat; a first syringe adapted for injecting the nanoparticle solution into a target area; and a second syringe or cannula adapted for aspirating melted fat from the target area after exposure of the target area to NIR light energy for period of time sufficient to melt the fat.

The combination of gold nanorods and NIR light to gentle melt and liquefy adipose and skin has not heretofore been disclosed. This combination offers unparalleled spatial and temporal control that no existing technique offers. The result is gentle fat melting, and minimal postoperative pain, by eliminating unnecessary damage to blood vessels and nerves. It is important to note that many of the prior art techniques emulsify fat, breaking it down into small globules—they do not melt fat. This has direct implications on how the fat can be removed. As a result, the inventive technique is expeditious and minimally invasive, eliminating the need to use larger, traumatizing cannulas that are inserted through small incisions. While other prior art methods do melt fat, they do so by heating methods (chromophore-dependent) that present a real risk of thermal damage to the skin surface and/or tissue surrounding the target site.

BRIEF DESCRIPTION OF THE DRAWINGS

FIGS. 3A and 3B are plots of wavelength versus absorption, where FIG. 3A shows absorption in the visible range and FIG. 3B shows absorption with the visible range removed.

FIG. 4 shows three photographs demonstrating the absence of melting under different laser heating conditions.

FIG. 9A shows total subcutaneous tissue in lipoaspirate, FIG. 9B shows free-acid fatty content in lipoaspirate, and FIG. 9C shows cell diameter in lipoaspirate.

DETAILED DESCRIPTION

Disclosed herein are a method and system which combine gold nanorods, near infrared light and minor medical procedures to reduce and remove fatty tissue. By injecting a small volume of a solution of gold nanorods into the targeted area, the invention provides for the selective melting of fat and the tightening of skin upon illumination using a low power, biologically benign Near Infrared (NIR) laser.

Figure 1:
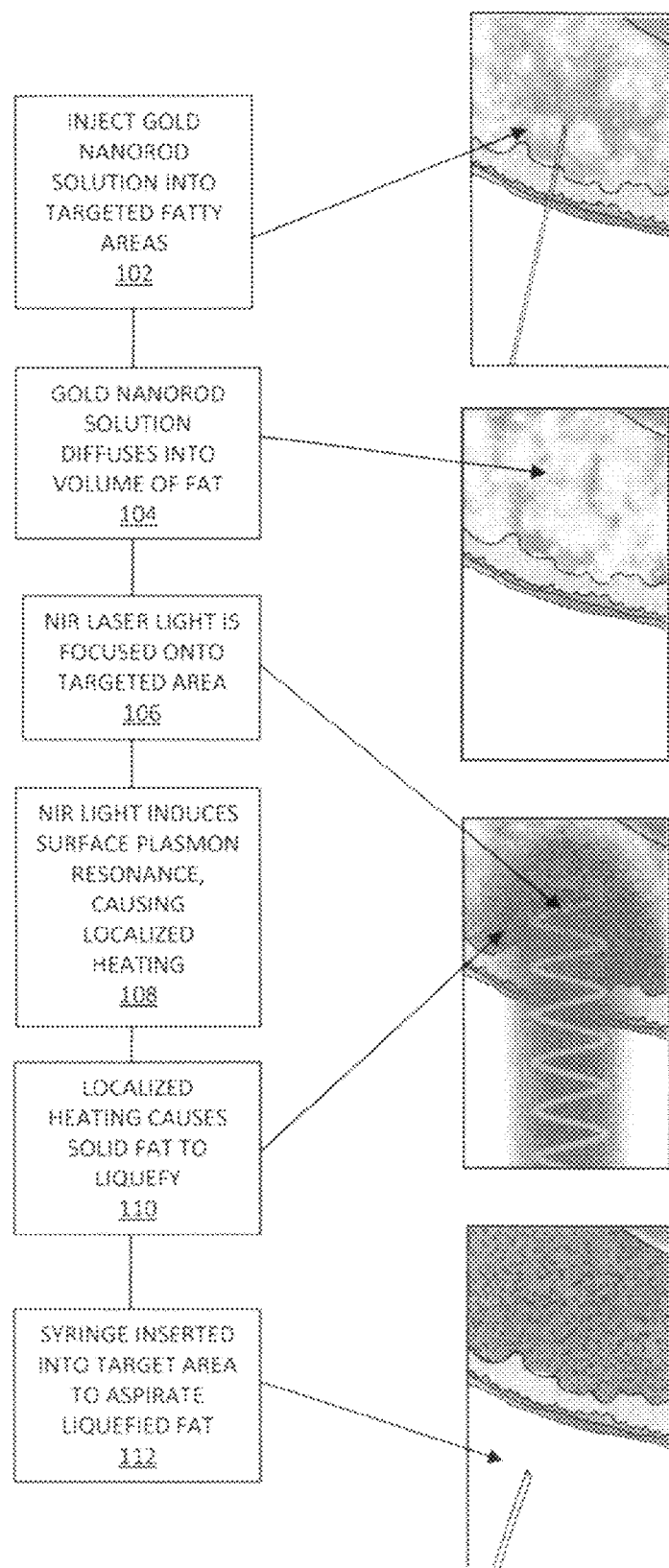
FIG. 1 illustrates an exemplary sequence of steps in a procedure for selective fat removal according to the present invention.

FIG. 1 illustrates the process flow for the inventive method, with each process step linked by an arrow to a diagrammatic image of the step as performed on a target area of a patient. The flexibility in the laser diameter, shape and intensity allows precise control over the target area, which may vary from very small, on the order of a few millimeters, to relatively large, e.g., several centimeters in diameter. In step 102, the physician administers a subcutaneous injection into the target area of a solution of gold nanorods (GNRs) suspended in a sterile, inert liquid, e.g., distilled water, using a fine syringe. In step 104, the GNR solution diffuses through the adipose tissue to be targeted. Immediately after injection, or as soon as practically possible, NIR laser light is focused onto the target area (step 106) for a period that may range from a few seconds to several minutes, depending on the area and volume of the targeted fat, and at least for a sufficient period of time to induce surface plasmon resonance within the GNRs. The laser light has a wavelength within the range of 600 nm to 950 nm, preferably within the range of 700 nm to 900 nm, and more preferably about 800 nm. In step 108, SPR is induced, producing localized heating which, in step 110, causes the solid fat to liquefy. Finally, in step 112, the physician inserts a syringe into the targeted area to aspirate the liquefied fat.

A similar procedure may be used to heat and thus stimulate the surrounding skin to minimize sagging after adipose tissue removal. In such a procedure, the GNR solution may be applied directly to the skin or injected intradermally prior to irradiation by the NIR laser light.

Figure 2:
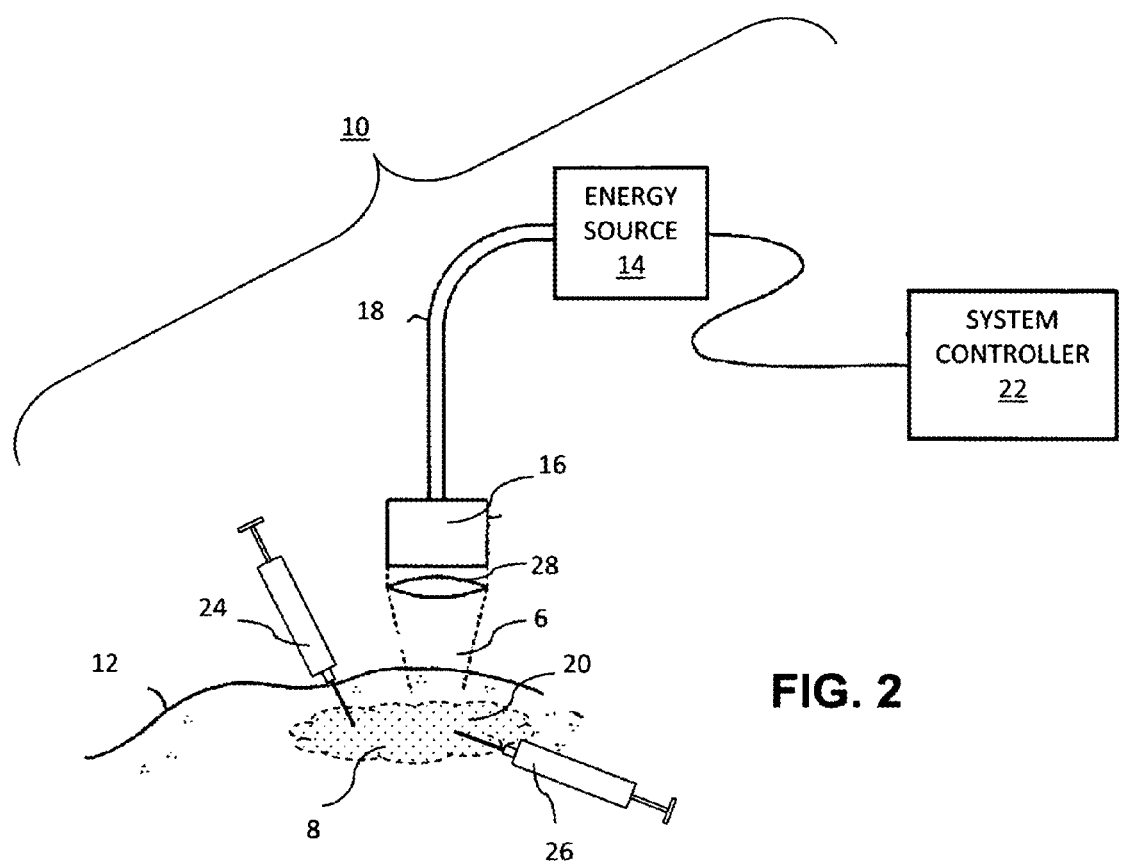
FIG. 2 is a diagrammatic view of a kit and apparatus for performing selective fat removal.

FIG. 2 is a representative schematic diagram of the components of the system 10 of the present invention. The GNRs 8 (in solution) are injected into the target tissue 20 using syringe 24. The GNRs are preferably suitable for in vivo use, for example, a polymer coating can be added for long circulation. The GNR's should be sterilized and certified endotoxin-free. The NIR laser energy 6 from the energy source 14 is directed into delivery device 16 via a delivery channel 18, which may be a fiber optic, articulated arm, or other appropriate optical waveguide. In preferred embodiments, the NIR laser is tunable to allow selection of a wavelength that is optimized for different size GNRs. The laser should preferably have adjustable power to modulate the degree of heating. Control system 22 provides a user interface for use by the physician, or assisting nurse or technician, to select the appropriate laser wavelength, intensity, duration and other parameters that may affect the treatment. At the distal end of delivery device 16 is an energy directing means 28 for directing the pulsed energy toward the surface tissue 12 overlying the target tissue (fat) 20. The directing means 28 may be one or more optical elements such as a lens or other focusing element, beam shaping optics, slits, apertures, gratings, an array of lenses and other optics or other focusing configuration, which focuses the beam within the targeted volume of fat containing the GNRs. In a preferred embodiment, the optical elements may include beam expanding lenses to allow adjustment of the beam spread to cover different size target areas. Following irradiation of the GNRs in the fatty tissue to liquefy the fat 20, the liquid is aspirated using syringe 26 that is inserted into the pocket of liquefied fat. The invention further includes a kit for performing selective fat removal in conjunction with an existing NIR laser unit. The kit includes the GNRs 8 in solution and syringes 24 and 26. The syringe for extracting the liquefied fat may be replaced by a fine cannula connected to a vacuum source that is capable of generating suction at the distal end of the cannula sufficient to draw the liquefied fat from the target area and into a collection vessel.

The inventive technique is possible because NIR light of low power is minimally absorbed by endogenous components in the body, such as skin, water, hemoglobin. Furthermore, low power near infrared light does not cause photodamage to tissue. NIR light is currently used for imaging using Indocyanine green (ICG), an FDA approved imaging agent able to absorb and emit in this region. While skin and adipose tissue do not absorb the NIR wavelengths, GNRs do, enabling fine tuning of the spatiotemporal parameters of heating.

Because the fat is actually liquefied, the inventive method for selective fat removal has the further advantage of being able to use needles or cannulas that are much smaller in diameter (on the order of 16 or 18 gauge) than those required for conventional liposuction, thus reducing patient discomfort, minimizing the risk of damage to surrounding tissue, reducing the risk of scarring and infection, and accelerating healing at the site of the procedure. Another major improvement over the prior art methods is the duration of treatment. The highly selective and rapid heating produced by the excited GNRs is capable of producing the desired results within minutes, in contrast with the multiple hours required by typical liposuction procedures.

The following examples demonstrate the principles used in the present invention.

Example 1

Photothermal Melting of Butter

To demonstrate the selective photothermal melting of fat, we performed experiments on a ~2 mm layer of butter sandwiched between two slides separated by a silicone spacer small. Gold nanorods (GNRs) were procured from Nanopartz™, specifically "Ntracker™ for in vivo Therapeutics" gold nanorods coated in a proprietary dense layer of hydrophilic polymers, with 10 nm axial diameter and 42 nm length. According to information provided by Nanopartz, at this aspect ratio, the plasmon absorption peaks are at 817 nm and 512 nm. Laser heating was conducted on butter samples with and without GNRs using an unfocused (~2 mm diameter) 800 nm beam from a Ti-Sapphire (100 fs, 80 MHz) laser. The GNR-butter samples were prepared from a mixture of 10 μL of $3\times10^{12}$ GNR/mL with ~50 mg of butter. Melting was monitored by visual inspection.

The melting point of butter is 32-38° C. and its specific heat is ~5 joules/g° C. This means that with the ~2 mm diameter beam at 800 nm at 0.45 W power (14 W/cm$^2$), the illuminated butter sample should heat at a rate of approximately 2 degrees every second. The input heat and resulting heating rate is likely less in actuality because of absorption of the microscope slide glass.

The butter sample used in these experiments shows no absorption in the region of the laser illumination wavelength, 800 nm, as shown in FIGS. 3A and 3B. The primary contribution to absorption is the fatty acids in the milk fat, which absorb in the visible range of the spectrum. The opacity of the sample limits the transmission of light through the butter so the optical density is high, as shown in the plot of FIG. 3A. If the contribution of the light scattering to the spectrum is removed, the absorption due to the butter can be better visualized, as shown in FIG. 3B.

Figure 5A:
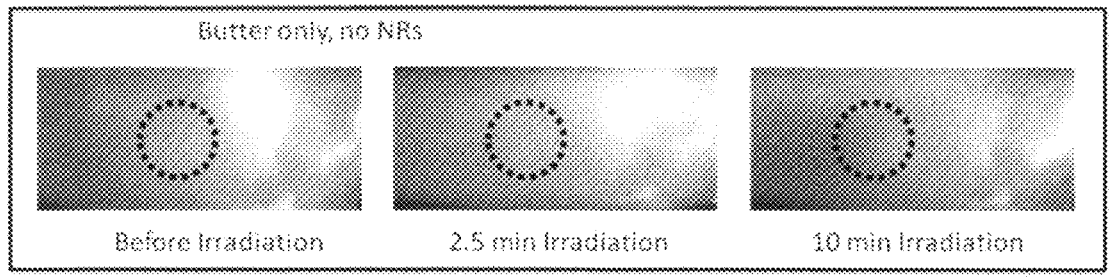
FIGS. 5A and 5B are photographs of butter samples before and after laser irradiation with and without gold nanorods, respectively.

Experiments on a plain butter sample showed that melting does not occur after 3 minutes, shown in the photos of FIG. 4, and up to 10 minutes, shown in FIG. 5A, of illumination with a 0.45 W laser beam.

Figure 5B:
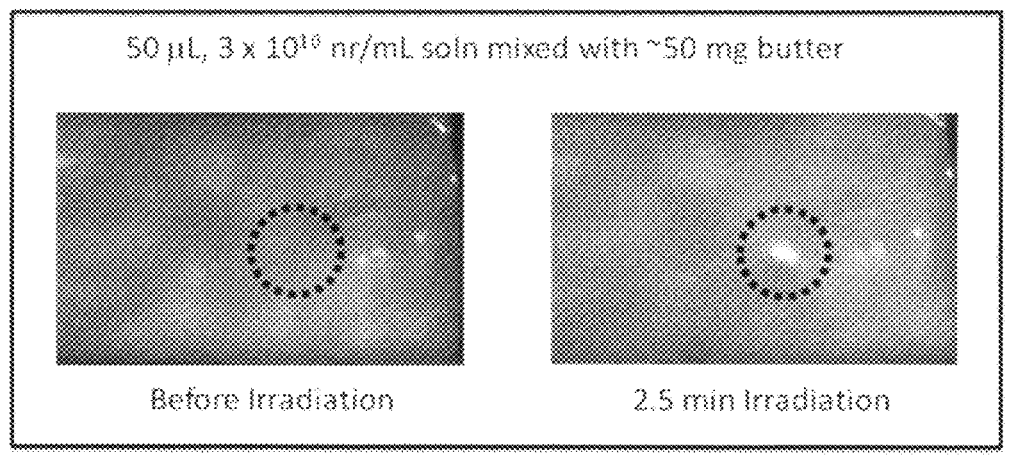

In the case of the GNR-butter sample under similar experimental conditions, melting of the butter was observed in the area irradiated by the NIR laser beam after 2.5 minutes of illumination. FIG. 5B shows the butter before and after irradiation.

Example 2

Photothermal Melting of Meat and Fat

Figure 6A:
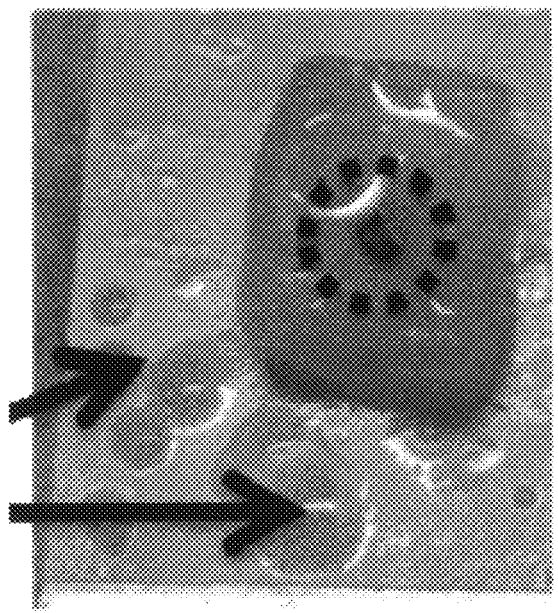
FIGS. 6A-6B are photographs of bacon fat samples with and without gold nanorods after exposure to NIR laser heating.
Figure 6B:
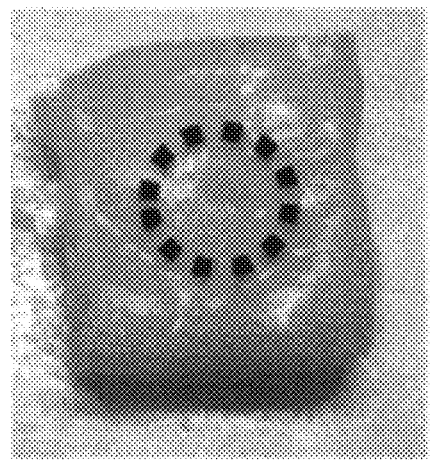
Figure 6C:
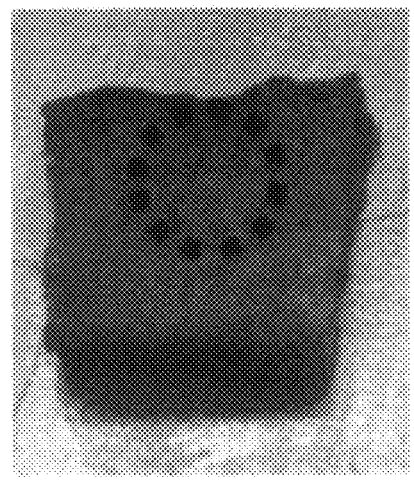
FIG. 6C is a photograph of bacon meat without gold nanorods after NIR laser irradiation.

Testing was also performed on bacon samples to compare the heating behavior in fat versus meat. We added 10 μl of $3\times10^{12}$ GNR/mL in water onto the fatty sections of the bacon and illuminated the treated sections with a ~2 mm diameter 800 nm beam at 2.5 W power. Melting of the GNR-injected fat was observed after 45 sec in the volume traversed by the laser beam where GNRs were present. Illumination was maintained for a total of 1.5 min to further melt the fat and determine whether charring can occur when high temperatures are attained. As shown in FIG. 6A, charring was observed. The melted fat (grease) became so hot that it splattered around the fat sample, indicated by the arrows in the figure. Control experiments on similarly irradiated non-GNR fat showed no melting (FIG. 6B). After irradiation, the fat had the same appearance as non-irradiated samples. The irradiated meat sections without GNRs were similarly unaffected (FIG. 6C). These results demonstrate the highly selective nature of the heating in the GNR-injected areas of fat versus untreated areas.

Experiments indicate that a GNR solution of within a range of $10^{11}$ to $10^{13}$ GNR/mL in water would be an effective injectable photothermal agent for melting adipose tissue upon irradiation with a NIR laser as a prelude to in-vivo fat removal. A preferred concentration range is on the order of $2 \times 10^{11}$ to $3 \times 10^{12}$. For the removal of 50 mL of fat, less than 10 mL of the GNR solution may be required. At the price of around $500 per liter of solution within the stated concentration range, the method provides an affordable alternative to conventional liposuction approaches.

Example 3

Ex Vivo Tissue Evaluation

GNR solution was produced, packaged and released in accordance with the FDA's current Good Manufacturing Practice guidelines by NanoSpectra BioSciences, Inc. (Houston, Tex.) following the literature. GNRs (10 nm×40 nm) were functionalized with poly(ethylene-glycol) (PEG) (5 kDa) via displacement of hexadecylcetyltrimethylammonium bromide (CTAB), a detergent used in the synthesis of GNRs. Proposed specifications for GNRs in the commercially produced NanoLipo™ system are summarized in Table 1 below.

TABLE 1

| Test | Procedure | Specifications |
|---|---|---|
| Absorption peak | UV/vis spectrophotometry | 800 ± 10 nm |
| Particle concentration | Transmission electron microscopy (TEM) | $1.6 \times 10^{13}$ NR/ml |
| Optical density at 800 nm | UV/vis spectrophotometry | 50 ± 5 OD |
| Dimensions | Transmission electron microscopy (TEM) | Length: 40 ± 5 nm Width: 10 ± 2 nm |
| CTAB concentration | ISO 2871-2: determination of cationic-active matter content | ≤4 µM |

Figure 7:
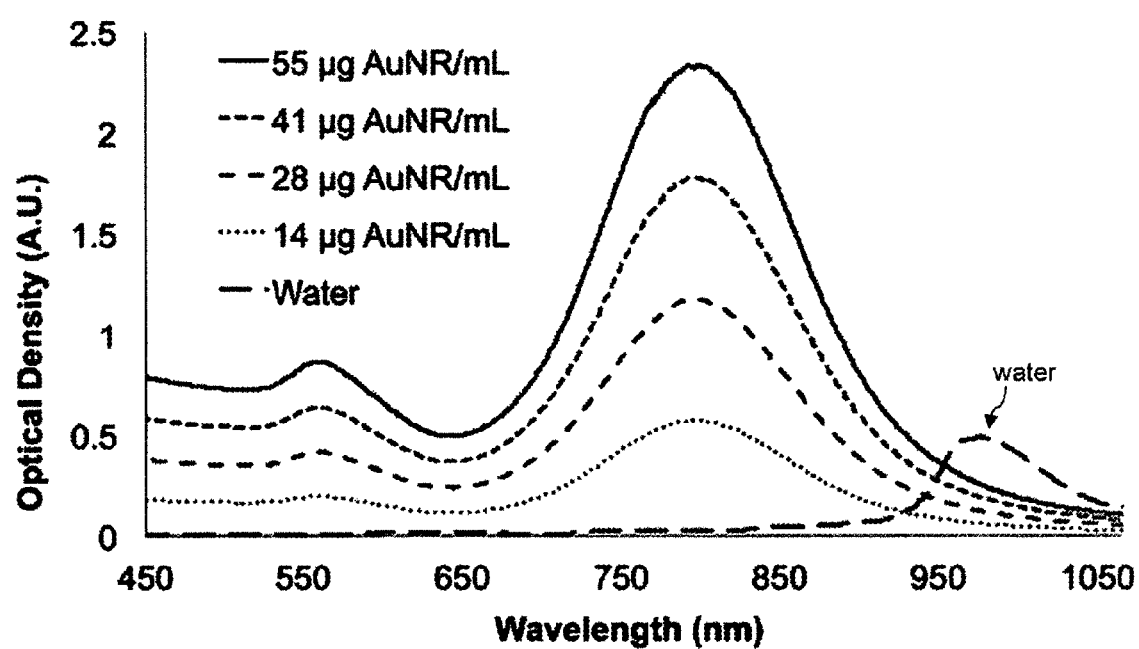
FIG. 7 is a plot of optical density versus wavelength for various concentrations of gold nanorods.

As shown by FIG. 7, the optical density of the GNR solution is tunable, ranging from a peak of about 0.5 A.U. for 14 µg of GNR/mL of water to 2.5 A.U. for 55 µg of GNR/mL of water. (Note that in the plot, "AuNR/mL" is the same as "GNR/mL".) The dimensions of the gold nanorods determine the peak absorption, which at every concentration is around 800 nm. The dashed line at the bottom of the plot shows the absorbance of water, which does not absorb at 800 nm, and peaks at around 980 nm.

The Lumenis LightSheer® Duet™ laser system (Lumenis, Yokneam, Israel), a commercially available, FDA-approved device with an 800 nm pulsed diode, was used for all studies. In general, in lasers used for cutaneous treatments, in addition to fluence, the variables that are adjusted to match the target are the pulse duration and the spot size. The pulse duration is adjusted to maximize the heating of the target area relative to surrounding structures, as proposed by the theory of selective photothermolysis. The spot size is chosen with multiple criteria: to match the size of the treatment area as closely as possible so as to minimize treatment time, and to achieve variable depth. Optimal heating can be achieved by altering not only fluence and pulse duration, but also by adjusting the spot size. It is known that small spot sizes require higher fluences to heat targets effectively. The effect of spot size on the depth of laser penetration is explained at least iii part by the phenomenon of dermal scattering. As a result, as spot size increases, the light penetrates deeper. Consequently, a larger spot size allows more effective heating, and conversely deeper heating can be achieved with lower fluences when delivered with a larger spot size. Spot sizes may range from around 9 mm×9 mm to around 35 mm×35 mm. Typical pulse durations can be in the range of around 30 ms to 60 ms, while fluences may range from around 4 J/cm$^2$ to 35 J/cm$^2$. In the current studies, the laser probe had an application area of 3.5 cm×2.2 cm, and was set to generate three consecutive 30 ms pulses with a fluence of 6 J/cm$^2$ (46 J/pulse) each pass (i.e., 138 J per pass before accounting for any attenuation by the tissue). In animal studies, the skin was cooled after a number of passes using a cool or cold compress, e.g., a damp towel or other cooling material, to keep skin surface temperatures below 42° C.

Ex vivo studies were performed on food-grade porcine abdominal tissue (pork belly). GNR or saline solution was injected into the experimental and control areas, respectively. Another region was treated with the laser only. The experimental and laser-only regions were exposed to 20 passes of the Lumenis laser. Frozen sections (10 µm) were stained with hematoxylin and eosin, prior to imaging using a Hamamatsu NanoZoomer 2.0HT slide scanning microscope.

Figure 8A:
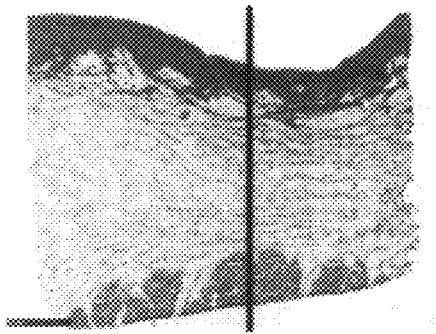
FIGS. 8A-8D are micrographs of ex vivo porcine skin and subcutaneous tissue illustrating the histological effects of the inventive procedure.
Figure 8B:
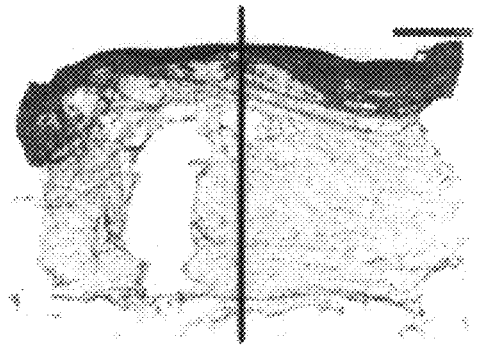
Figure 8C:
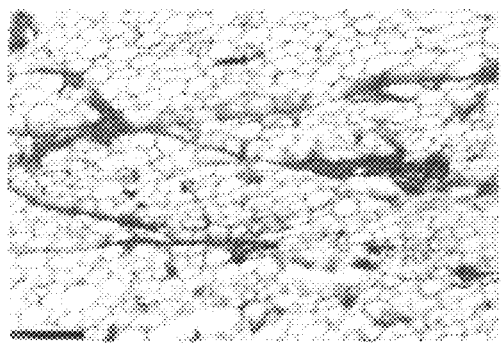
Figure 8D:
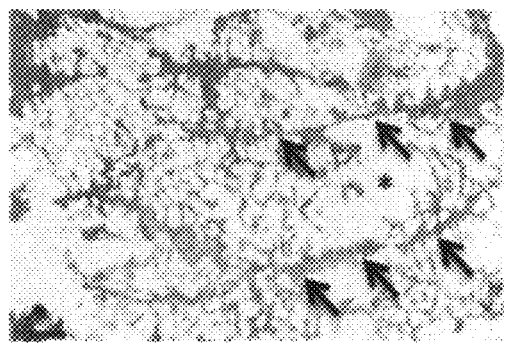

Porcine tissue was subcutaneously injected with GNR solution (0.1 g/L) and irradiated with a laser (800 nm, 2.5 kJ total, 30 ms/pulse), injected with GNR solution only, irradiated without GNRs, or left untreated as a control. In the absence of GNR solution, histology showed no signs of significant lipolysis (FIGS. 8A and 8C). Skin surface temperature was monitored and did not exceed 45° C. in the GNR-treated samples. GNR-treated regions appeared more translucent than regions treated with laser alone, suggesting liquefaction of fat. The tissue was also mechanically softer when probed with tweezers. Histology revealed disruption, apparent as voids, in subcutaneous adipose tissue but not in the dermal layer or connective tissue of GNR-treated samples (FIGS. 8B and 8D). Disruption of adipose tissue in these samples made them noticeably more fragile and difficult to section. Dermal and connective tissues in the GNR-treated samples appeared similar to those of untreated samples.

Example 4

Pharmacokinetics and Biodistribution of GNRs

Zucker rats were fed an unrestricted diet to maximize body fat content. Abdominal hair on the animals was trimmed using clippers and removed using a commercial depilatory such as NAIR™ (Church & Dwight Co, Inc., Ewing, N.J.). Following sterilization with surgical betadine, two regions were tattooed for conventional SAL or the inventive GNR-based procedure. During all procedures, surface skin temperature was monitored by a FLIR E50 infrared thermal camera.

Lateral subdermal tissue was infused with 1 mL of GNR solution (NanoSpectra solution diluted to 87.5 µg/mL). In one group of rats, the infused area was subjected to liposuction (SAL or GNR-based); in controls, no surgical procedure was performed. An untreated baseline group was also included. Blood was periodically collected via the tail for the first 48 hours. Rats were weighed and sacrificed at 24 hours, 48 hours, and 30 days post-operation and whole organs (spleen, liver, kidney, heart, lungs, brain, skeletal muscle, lipoaspirate, and treated region) were harvested and homogenized using zirconia/silica 2.3 mm diameter beads.

Gold content was measured in each organ by inductive coupled plasma-mass spectrometry (ICP-MS) following tissue dissolution in concentrated $HNO_3$ (67-69%) for five days. Fat-rich tissue required special processing, and was heated at 65° C. for 3 hours or until the solution became clear, indicating complete digestion. 175 µL of each solution was diluted to 4 mL, filtered (0.2 µm pores), and analyzed using a ThermoQuest Element 2 high-resolution ICP-MS machine.

PEG-coated GNRs in GNR-solution are essentially innocuous and the injected dose was below the LD50 of GNRs. The pharmacokinetics and toxicity of GNRs were examined in Zucker rats by ICP-MS at 24 and 48 hour post-subcutaneous injection; the extent of gold removal by liposuction was assessed by comparison to rats in which fat was not removed following GNR injection. In rats in which no liposuction was performed, we immediately observed evidence of gold accumulation in the liver, with approximately the same levels at 24 and 48 hours (7±2%). In rats treated with liposuction, the amount of gold remaining in all tissues was 34±16% lower than the injected dose. In these rats, the level of gold in the liver was very low at 24 h (<5%) but GNRs appeared to redistribute from the treated area to the liver at 48 h, to a level comparable to animals with no liposuction. Total recovered gold from all organs, including tissue removed by liposuction, nearly equaled the amount injected in all cases. In untreated rats, no gold was detected. Furthermore, ICP-MS of organs at 30 days showed that residual gold was present at greater levels in the kidneys (2%) than at 24 and 48 h (0%). Rats were weighed weekly to detect any GNR-induced weight loss, which could indicate toxicity. No significant weight loss was observed in rats treated with either the GNR-based procedure or conventional SAL up to 1 month.

Example 5

Procedure Efficacy in Yucatan Mini Pigs

We next examined whether the inventive procedure enhances fat removal relative to standard liposuction techniques using Yucatan mini pigs, whose soft tissue structure is more similar than smaller animals' to that of humans. The pigs were fed a standard diet with three meals per day. Procedures were performed on two abdominal regions on each pig.

Abdominal hair was trimmed using clippers and removed using a commercial depilatory such as NAIR™ (Church & Dwight Co, Inc., Ewing, N.J.). Following sterilization with surgical betadine, two regions were tattooed for conventional SAL or the inventive GNR-based procedure. During all procedures, surface skin temperature was monitored by a FUR E50 infrared thermal camera.

GNR solution was mixed with anesthetic tumescent solution (Ringer's solution saline with 0.1% lidocaine, 1 ppm epinephrine) to a concentration of $2.5\times10^{11}$ GNR/mL (14 µg GNR/mL). 100 mL of the solution was injected into adipose tissue through a small stab incision in a systematic fan pattern to ensure uniform permeation and distribution in the target region (5 cm×5 cm). The laser (spot size~2.3 cm×3.5 cm) was applied to the marked area over the course of 5±1 min (approximately twenty-four passes) to deliver 1000-2000 J of energy, alternating the orientation of the laser application probe to ensure complete coverage of the area. (Note that this is less than the ~10 minute optimal wait time for lidocaine and epinephrine to take effect before initiating conventional SAL.) The skin was cooled using a wet towel every four passes to maintain a safe skin temperature, as verified by the thermal imaging camera (FLIR E50, FLIR, Wilsonville, Oreg.). Subcutaneous tissue was removed by suction-assisted liposuction (Gomco OptiVac® G180, Allied Healthcare Products, St. Louis, Mo.) and the incision was closed using an absorbable suture, while the operated areas were marked with a non-absorbable suture.

Lipoaspirates were centrifuged at 1000 rpm for 5 min to separate the liquid phase, including injection solution, from solid subcutaneous tissue. Both phases were weighed, and subcutaneous tissue was examined under dark field microscopy at 10× magnification. Cell diameters (along the longest axis, all cells in each field of three representative images, totaling~50 cells) were measured using ImageJ software. To quantify the proportion of removed subcutaneous tissue consisting of free fatty acids and glycerol, 1 g of each subcutaneous tissue sample was digested with 3 mg collagenase/dispase following manufacturer protocol for 1 hour at 37° C. (Roche) and centrifuged (2000 rpm, 5 min) to produce three distinct layers (from top to bottom: free fatty acids and glycerol, adipocytes, and fibrous matter). The percentage of removed tissue consisting of free fatty acids and glycerol was determined by measuring the volume of the upper layer containing secreted fatty acids and glycerol, converting it to mass (assuming 1 mL=1 g), and dividing by the total mass of removed tissue.

Ultrasound measurements were taken using a Biosound MyLab30Vet machine with a LA435 Linear Probe 18-10 MHz transducer through a thick layer of ultrasound gel before, immediately after, and at 10 days, one month, two months, and three months post-procedure to monitor changes in tissue depth. User pressure did not affect measurements of adipose layer thickness, as no significant difference was detected between measurements collected at maximum (gentle) pressure and the moment just before the transducer detached from the surface following release of pressure. Additionally, images were acquired during exhalation to account for any changes in depth due to breathing. Images parallel and perpendicular to the spinal axis of the animal were acquired to obtain complete coverage of the operated area. The machine was set to measure the same depth for all time points for each region.

In each image, the distance from the top of the deep fascial membrane to the top of the superficial fascial membrane, which appears white on ultrasound, was measured at four cross-sections spaced 1 cm apart in each ultrasound image (five images per treated region) using ImageJ. Images in which resolution was too low to identify fascial membranes (fewer than 10% of images) were not analyzed. Each measured distance is plotted to illustrate the change in average depth over time. Interpretation of ultrasound was aided by compression testing during image collection; fat layers compressed more than fibrous layers.

Skin appearance was assessed by ruler measurement and photography. Continuous variables, except for adipose thickness measured by ultrasound, are reported as means and standard errors. Groups were compared by two-tailed student's t-test in Microsoft Excel 2010.

Figure 9A:
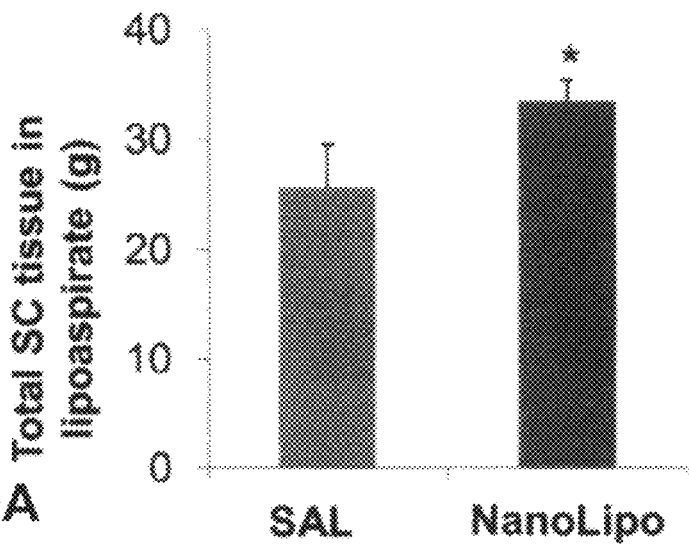
FIGS. 9A-9C are histograms comparing results of the inventive procedure with standard suction-assisted lipectomy (SAL), where
Figure 9B:
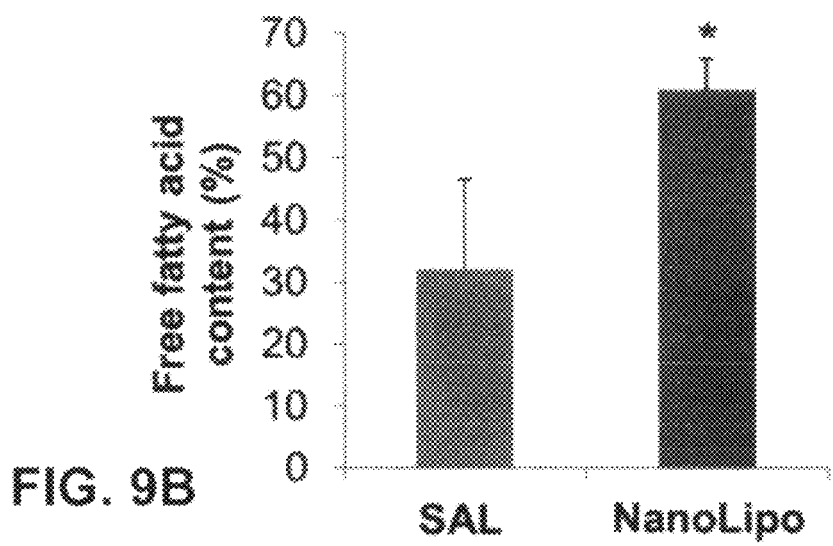
Figure 9C:
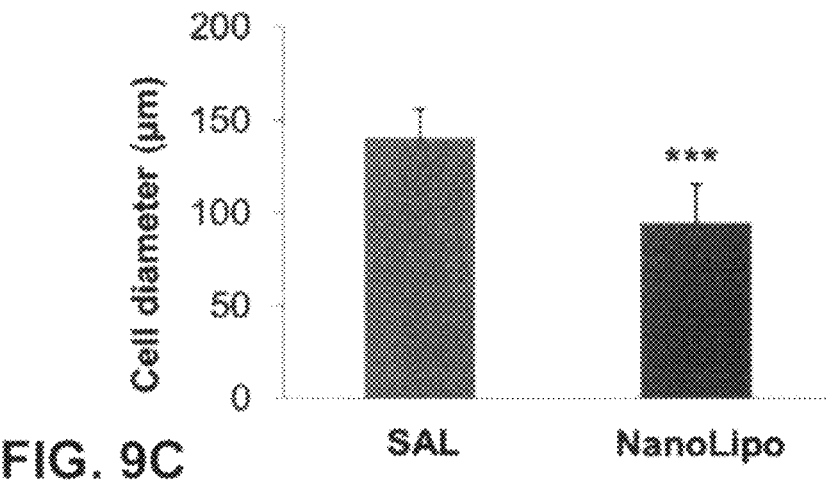
Figure 9D:
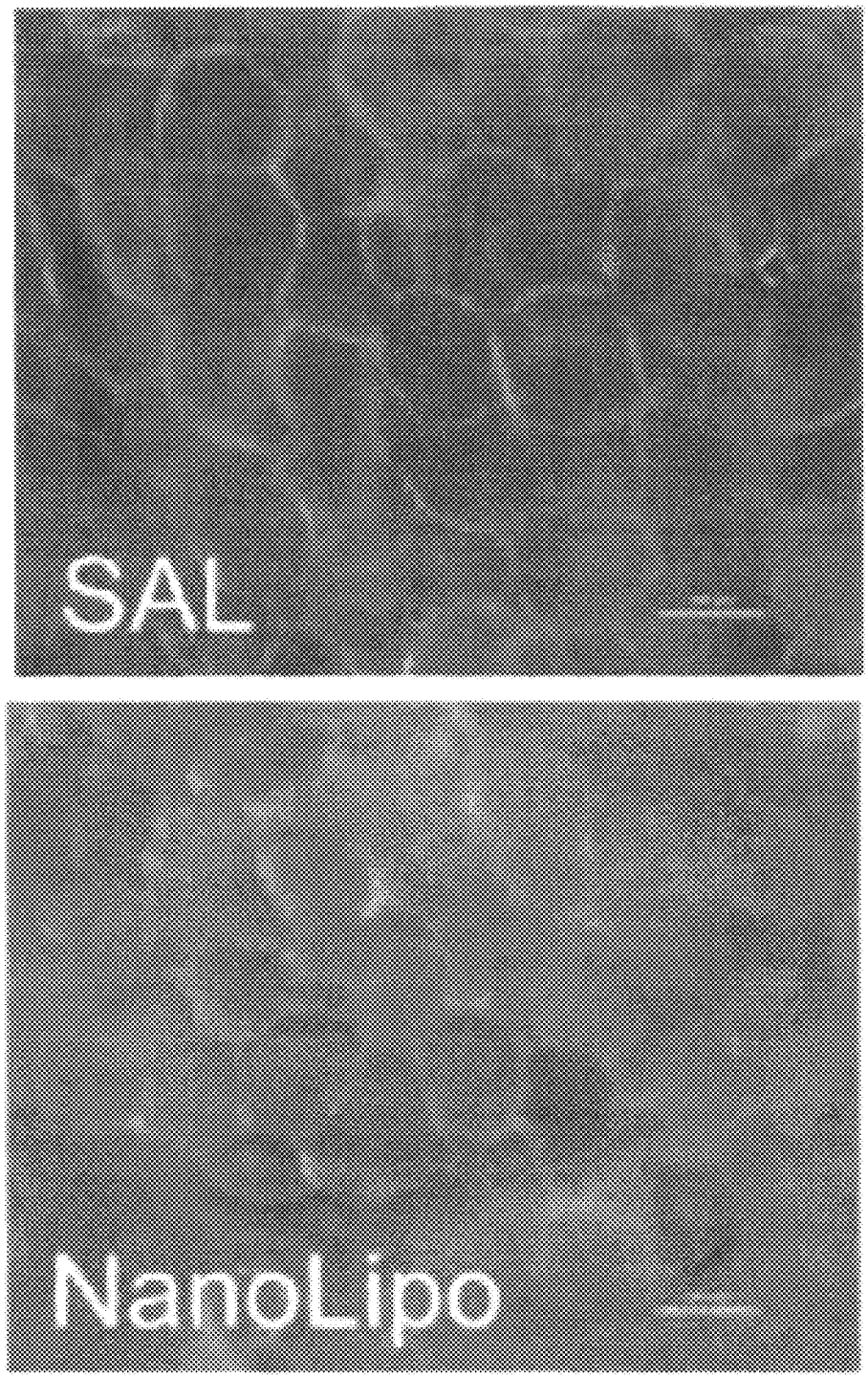
FIG. 9D is a set of dark-field micrographs of tissue following SAL and the inventive procedure.

The inventive GNR-based technique, also known as "NanoLipo™", allowed removal of considerably more subcutaneous tissue (FIG. 9A) and fat than conventional SAL in a comparable amount of time. Further, the NanoLipo™ procedure required much less time (4 min vs. 10 min) to remove a similar volume of lipoaspirate while causing less bruising than SAL. Collagenase digestion and centrifugation revealed that the fatty content of tissue removed following the NanoLipo™ procedure was nearly twice that following SAL (FIG. 9B). As photothermolysis may trigger release of fatty acids and glycerol from adipocytes, which would reduce their diameter, we compared the diameter of adipocytes in lipoaspirates following each procedure by dark field microscopy and image analysis using ImageJ software. Adipocytes in lipoaspirates following NanoLipo™ treatment were significantly smaller than those in lipoaspirates following SAL, as shown in FIG. 9C. The dark field micrographs of FIG. 9D further illustrate the difference in the average diameter of adipocytes for the GNR-based and conventional SAL procedures.

Example 6

Assessment of Tissue Depth Using Ultrasound

Figure 10A:
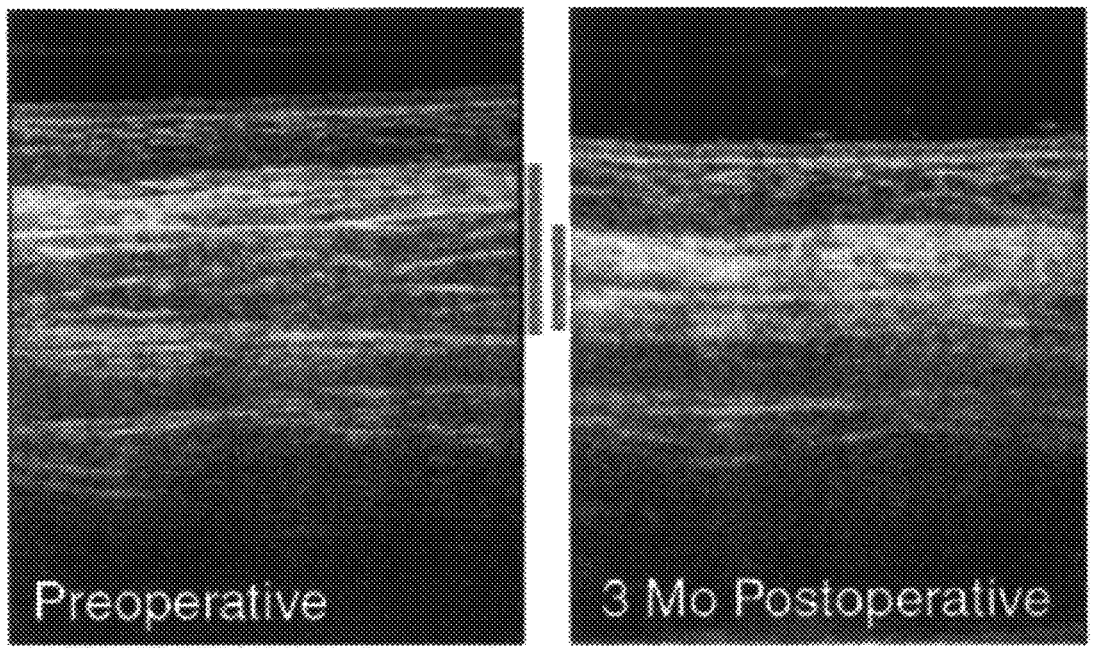
FIGS. 10A and 10B are representative ultrasound images prior to and 3 months post-treatment using the inventive method (FIG. 10A) and SAL (FIG. 10B), with the vertical lines indicating the adipose layer targeted by the procedure.
Figure 10B:
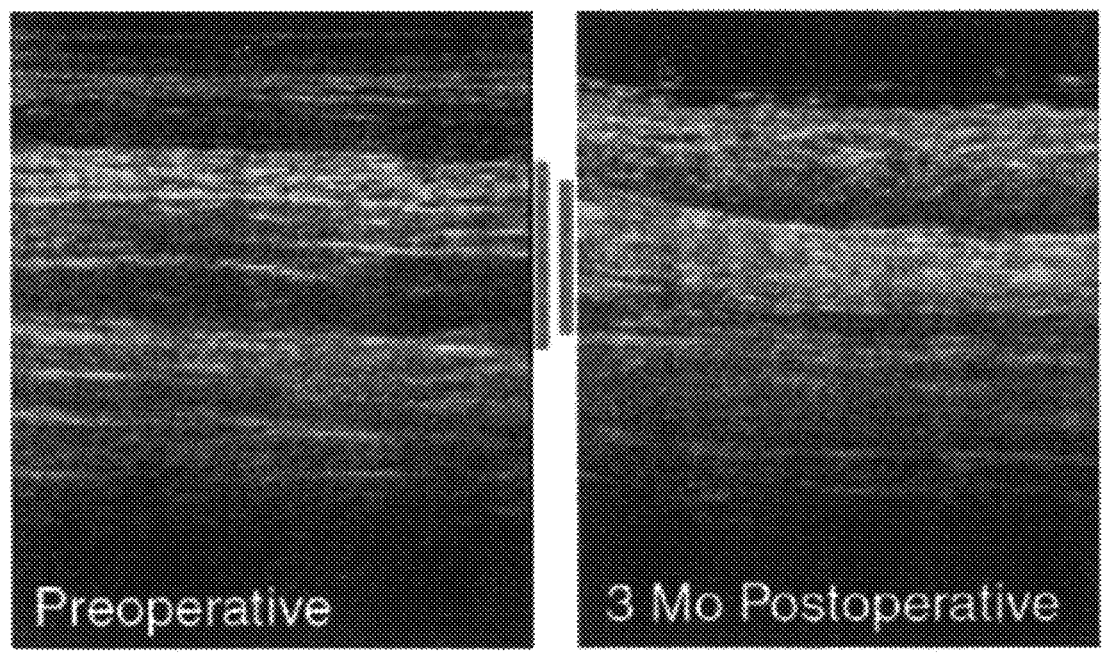
Figure 10C:
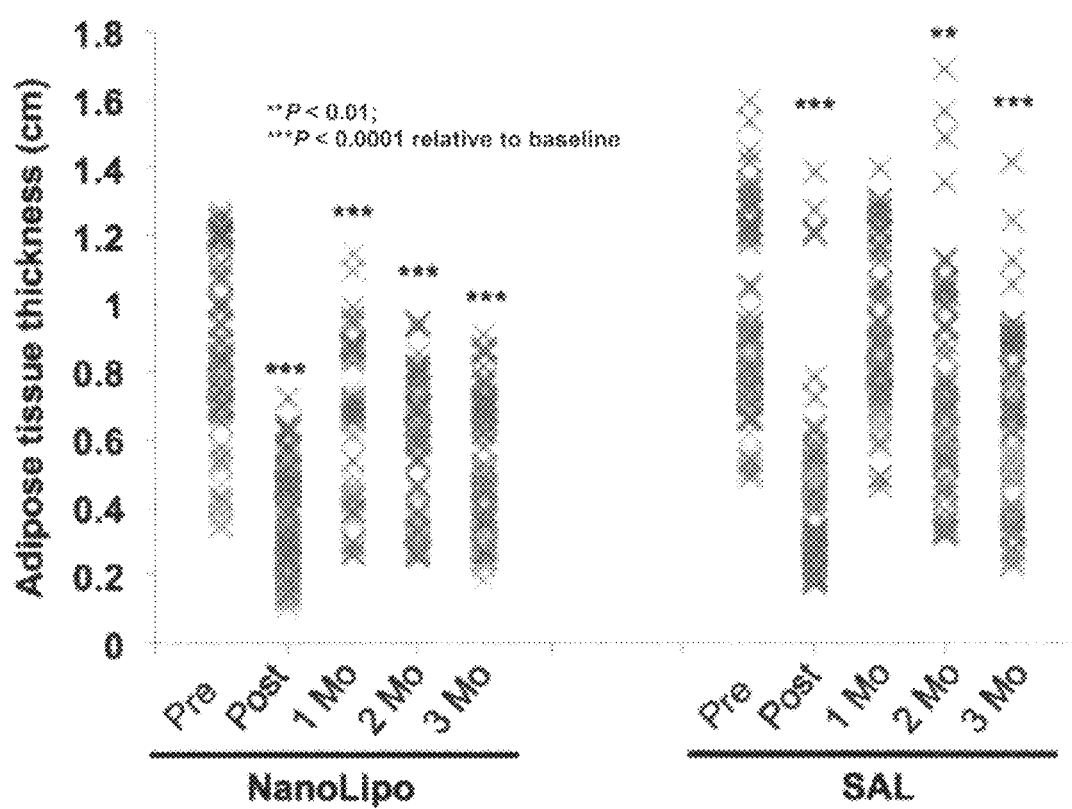
FIG. 10C plots the quantified tissue thickness for the inventive procedure (left) and SAL (right) for 3 pigs based on 20 measurements per procedure.

To assess whether the NanoLipo™ procedure enhances reductions in adipose tissue thickness and yields more uniform results relative to conventional SAL, we measured the thickness of the superficial adipose layer before and immediately after the procedure, as well as at 1, 2, and 3 months post-operation using ultrasound. The resulting images are shown in FIGS. 10A and 10B for the GNR-based procedure and SAL, respectively. Analysis of ultrasound images reveals comparable depth changes between the NanoLipo™ treatment and SAL immediately post-operation. FIG. 10C plots the quantification of tissue thickness for three separate procedures, NanoLipo™ (left) and SAL (right), performed on three pigs, with 20 measurements per procedure. These results correlate well with the total volume of subcutaneous tissue removed, shown in FIG. 9A. The change in superficial adipose thickness at one month post-surgery is significant in NanoLipo™ method treated areas but not in those treated using SAL, suggesting that either less swelling occurs, or that swelling subsides faster, with localized thermally-aided fat removal. While we cannot compare adipose tissue thickness across surgical procedures because of differences in normalization, the inventive GNR-based technique appears to provide greater reductions in thickness at 3 months post-surgery, as evidenced by FIGS. 10A and 10B. Tissue depth reduction is more uniform in NanoLipo™-treated regions than in those treated with SAL across all time points, as evidenced by a tighter distribution of thicknesses shown in FIG. 10C.

The application of the inventive technology has many secondary benefits in addition to the cosmetic effect of eliminating body fat. For example, illnesses such as diabetes mellitus are directly related to fat storage and obesity. Insulin resistance can be eliminated by reducing body fat content. This scientific fact has significant implications on chronic illnesses such as diabetic nephropathy, diabetic retinopathy and coronary heart disease. To date, existing techniques have not exhibited the ability to remove an effective amount of fatty tissue without causing severe damage to adjacent tissue. In addition, during existing procedures, patients are exposed to the potentially dangerous effects of lidocaine toxicity, which is included in current tumescent solutions.

The controlled thermal melting of fat protects all other vital structures, reducing post operative pain and, hence, reducing the amount of lidocaine needed in a tumescent solution and avoid life-threatening risks of lidocaine toxicity. The fact that no-to-minimal mechanical force is required to practice the inventive technique further eliminates the risk of penetrating deep tissues. Penetration of tissues such as bowels, livers and lungs has been reported in the literature with use of excessive force to achieve adequate liposuction.

Selecting an appropriate laser pulse length, among other parameters, allows the inventive GNR-based procedure to precisely increase the amount of energy conveyed to the target, i.e., adipose tissue. The major advantage of this technology is a consequence of the addition of exogenous energy absorbers (GNRs) rather than relying on endogenous elements, such as water. Test results strongly suggest that the NanoLipo™ procedure aids in removal of adipose tissue while maintaining the integrity of surrounding tissues. Although the inventive approach involves an additional laser step compared to SAL, in SAL the surgeon must wait 10 min for the tumescent solution to take effect. Because the laser can already be applied during this period, the GNR-based approach requires no more time than SAL. Importantly, the NanoLipo™ technique accelerates fat removal during the liposuctioning step because of photothermal fat melting.

In addition, since GNRs do not bind to tissue, a large portion of injected GNRs are immediately removed by aspiration. Since the concentrations delivered (0.01-0.05 g/kg body weight) are well below the expected toxicity limit (3.2 g/kg) for gold, long-term GNR exposure is not expected. In combination with the temporary nature of the mechanical changes induced by selective photothermolysis, the NanoLipo™ procedure should be well-tolerated

REFERENCES

Incorporated Herein by Reference as Part of the Disclosure

1. R. Weissleder, "A clearer vision for in vivo imaging", *Nat. Biotech.* 19 (2001) 316-317.
2. S. J. Oldenburg, et al., "Infrared extinction properties of gold nanoshells", *Appl. Phys. Lett.* 75 (1999) 2897-2899.
3. L. R. Hirsch, et al., "Nanoshell-mediated near-infrared thermal therapy of tumors under magnetic resonance guidance", *Proc. Natl. Acad. Sci. U.S.A.* 100 (2003) 13549-13554.
4. Y. N. Xia, et al., "One-dimensional nanostructures: synthesis, characterization, and applications", *Adv. Mater.* 15 (2003) 353-389.
5. V. P. Zharov, et al., "Photothermal detection of local thermal effects during selective nanophotothermolysis", *Appl. Phys. Lett.* 83 (2003) 4897-4899.
6. J. Lee, et al., "Nanoparticle assemblies with molecular springs: a nanoscale thermometer", *Angew. Chem. Int. Ed.* 44 (2005) 7439-7442.
7. W. Huang, et al., "Gold nanoparticles propulsion from surface fueled by absorption of femtosecond laser pulse at their surface plasmon resonance", *J. Am. Chem. Soc.* 128 (2006) 13330-13331.
8. H. Takahashi, et al., "Gold nanorod-sensitized cell death: microscopic observation of single living cells irradiated by pulsed near-infrared laser light in the presence of gold nanorods", *Chem. Lett.* 35 (2006) 500-501.
9. J. Y. Chen, et al., "Immuno gold nanocages with tailored optical properties for targeted photothermal destruction of cancer cells", *Nano Lett.* 7 (2007) 1318-1322.
10. J. Chen, et al., "Gold nanocages: bioconjugation and their potential use as optical imaging contrast agents", *Nano Lett.* 5 (2005) 473-477.
11. P. K. Jain, et al., "Calculated absorption and scattering properties of gold nanoparticles of different size, shape, and composition: applications in biological imaging and biomedicine", *J. Phys. Chem. B* 110 (2006) 7238-7248.
12. S. Link, et al., "Shape and size dependence of radiative, non-radiative and photothermal properties of gold nanocrystals", *Int. Rev. Phys. Chem.* 19 (2000) 409-453.
13. B. G. Prevo, et al., "Scalable routes to gold nanoshells with tunable sizes and response to near-infrared pulsed-laser irradiation", *Small* 4 (2008) 1183-1195.
14. G. Wu, et al., "Remotely triggered liposome release by near-infrared light absorption via hollow gold nanoshells", *J. Am. Chem. Soc.* 130 (2008) 8175-8177.
15. D. V. Volodkin, et al., "Near-IR remote drug release from assemblies of liposomes and nanoparticles", *Angew. Chem. Int. Ed.* 48 (2009) 1807-1809.
16. X. H. Huang, et al., "Plasmonic photothermal therapy (PPTT) using gold nanoparticles", *Laser Med. Sci.* 23 (2008) 217-228.
17. Lynch, D. J., et al., "Practice advisory on liposuction", *Plast. Reconstr. Surg.* 113: 1478; discussion 1491; discussion 1494, 2004.
18. Beran, S. J., et al., "Body contouring (overview)", *Select. Read. Plast. Surg.* 8: 1, 1998.
19. Weniger, F. G., et al., "Liposuction of the legs and ankles: A review of the literature", *Plast. Reconstr. Surg.* 113: 1771, 2004.
20. Pitman, G. H., "Liposuction and body contouring", In S. J. Aston (Ed.), *Grabb and Smith's Plastic Surgery*, 5th Ed. Philadelphia: Lippincott-Raven, 1997.
21. Fodor, P. B., et al., "Wetting solutions in ultrasound-assisted lipoplasty", *Clin. Plast. Surg.* 26: 289, 1999.
22. Klein, J. A., "Tumescent technique for local anesthesia improves safety in large-volume liposuction", *Plast. Reconstr. Surg.* 92: 1085, 1993.
23. Pitman, G. H., et al., "Tumescent liposuction", *Clin. Plast. Surg.* 26: 289, 1999.
24. Rubinstein, E. F., "An anesthesiologist's perspective of lipoplasty", *Clin. Plast. Surg.* 26: 423, 1999.
25. Brown, S. A., et al., "Pharmacokinetics and safety of epinephrine use in liposuction", *Plast. Reconstr. Surg.* 114: 756, 2004.
26. Friedberg, B. L., "Liposuction 'conscious sedation' monitored anesthesia care and level of consciousness monitoring (Letter)", *Aesthetic Plast. Surg.* 29: 59, 2005.
27. Rohrich, R. J., et al., "The role of subcutaneous infiltration in suction-assisted lipoplasty: A review", *Plast. Reconstr. Surg.* 99: 514, 1997.
28. Commons, G. W., et al., "Large-volume liposuction: A review of 631 consecutive cases over 12 years", *Plast. Reconstr. Surg.* 108: 1753, 2001.
29. Horton, J. B., et al., "Patient safety in the office-based setting", *Plast. Reconstr. Surg.* 117: 61e, 2006.
30. Keyes, G. R., et al., "Analysis of outpatient surgery center safety using an internet-based quality improvement and peer review program", *Plast. Reconstr. Surg.* 113: 1760, 2004.
31. Trott, S. A., et al., "Safety considerations and fluid resuscitation in liposuction: An analysis of 53 consecutive patients", *Plast. Reconstr. Surg.* 102: 2220, 1998.
32. Fodor, P. B., "Power-assisted lipoplasty versus traditional suction-assisted lipoplasty: Comparative evaluation and analysis of output (Letter)", *Aesthetic Plast. Surg.* 29: 127, 2005.
33. Gingrass, M. K., "Lipoplasty complications and their prevention", *Clin. Plast. Surg.* 26: 341, 1999.
34. Kim, J., et al., "Abdominoplasty, liposuction of the flanks, and obesity: Analyzing risk factors for seroma formation", *Plast. Reconstr. Surg.* 117: 773, 2006.
35. Rohrich, R. J., et al., "The key to long-term success in liposuction: A guide for plastic surgeons and patients", *Plast. Reconstr. Surg.* 114: 1945, 2004.

The invention claimed is:

1. A method for selective removal of fat from a target area in a subject in need thereof, comprising:
   injecting a solution of photo-absorbing nanoparticles in a pattern to define a uniform distribution of injected solution in adipose tissue in the target area, wherein the solution comprises gold nanorods suspended in water at a concentration range of $10^{11}$ to $10^{13}$ GNR/mL;
   delivering a series of pulses of near infrared light across an area of skin overlying the target area and into the injected solution for an exposure duration to induce surface plasmon resonance in the nanoparticles, wherein the near infrared light has a combination of optical parameters selected from the group consisting of beam energy, pulse duration, emission wavelength within a range of 700 to 900 nm, emission intensity, beam focus and beam area, the optical parameters and the exposure duration selected to excite the nanoparticles to liquefy fat within the target area; and
   aspirating a liquid from the target area, the liquid comprising subcutaneous tissue, liquefied fat, and the injected solution.

2. The method of claim 1, wherein the step of delivering comprises scanning the near infrared light across the target area using a plurality of passes.

3. The method of claim 2, further comprises applying a cooling material to the area of skin overlying the target area after a subset of the plurality of passes.

4. The method of claim 1, wherein the emission wavelength is 800 nm±10 nm.

5. The method of claim 1, wherein the nanoparticles have an aspect ratio in the range of 1:3-1:5.

6. The method of claim 1, wherein the nanoparticles have an axial diameter of approximately 10 nm and a longitudinal diameter in the range of 9 to 50 nm.

7. The method of claim 1, wherein the nanoparticles have a length of 40±5 nm and a width of 10±5 nm.

8. The method of claim 1, wherein the solution further comprises an anesthetic tumescent solution.

9. The method of claim 1, wherein the nanoparticles are functionalized with poly(ethylene-glycol).

10. The method of claim 1, wherein the beam area is within a range of 9 mm×9 mm to 35 mm×35 mm.

11. The method of claim 10, wherein the beam area is 2.3 cm×3.5 cm.

12. The method of claim 1, wherein the beam energy is in a range of 1000 to 2000 J.

13. The method of claim 1, wherein the pulse duration is within a range of 30 ms to 60 ms.

14. A method of tightening skin around the target area according to claim 1.

15. A method for subcutaneous fat removal and skin tightening in a person in need thereof, the method comprising:
   subcutaneously injecting a suspension of photo-absorbing gold nanorods in solution into a target region of adipose tissue of the person, wherein the nanorods have an aspect ratio in the range of 1:3 to 1:5;
   scanning pulses of NIR light energy for a plurality of passes across an area of skin overlying the target region and into the injected suspension for an exposure duration, the NIR light energy having optical parameters selected from the group consisting of beam energy, pulse duration, emission wavelength within a range of 700 to 900 nm, emission intensity, beam focus and beam area, the optical parameters and the exposure duration selected to excite the nanoparticles to liquefy fat within the target region; and extracting a liquid from the target region, the liquid comprising subcutaneous tissue, liquefied fat, and the injected suspension.

16. The method of claim 15, further comprises applying a cooling material to the area of skin overlying the target region after a subset of the plurality of passes.

17. The method of claim 15, wherein the emission wavelength is 800 nm±10 nm.

18. The method of claim 15, wherein the gold nanorods have an axial diameter of approximately 10 nm and a longitudinal diameter in the range of 9 to 50 nm.

19. The method of claim 15, wherein the gold nanorods have a length of 40±5 nm and a width of 10±5 nm.

20. The method of claim 15, wherein the suspension has a concentration of $10^{11}$ to $10^{13}$ GNR/mL in water.

21. The method of claim 20, wherein the suspension further comprises an anesthetic tumescent solution.

22. The method of claim 15, wherein the gold nanorods are functionalized with poly(ethylene-glycol).

23. The method of claim 15, wherein the beam area is within a range of 9 mm×9 mm to 35 mm×35 mm.

24. The method of claim 23, wherein the beam area is 2.3 cm×3.5 cm.

25. The method of claim 15, wherein the beam energy is in a range of 1000 to 2000 J.

26. The method of claim 15, wherein the pulse duration is within a range of 30 ms to 60 ms.

* * * * *